(12) United States Patent  
Yamaguchi (10) Patent No.: US 7,109,507 B2  
(45) Date of Patent: Sep. 19, 2006

(54) OPTICAL OBJECT IDENTIFYING DEVICE AND PRINTING APPARATUS

(75) Inventor: Akifumi Yamaguchi, Kashiba (JP)

(73) Assignee: Sharp Kabushiki Kaisha, Osaka (JP)

( * ) Notice: Subject to any disclaimer, the term of this patent is extended or adjusted under 35 U.S.C. 154(b) by 0 days.

(21) Appl. No.: 10/928,180

(22) Filed: Aug. 30, 2004

(65) Prior Publication Data

US 2005/0051743 A1   Mar. 10, 2005

(30) Foreign Application Priority Data

Sep. 8, 2003   (JP) .......................... P2003-315059

(51) Int. Cl.  
    *G01N 21/32*   (2006.01)
(52) U.S. Cl. ............... 250/559.16; 356/237.3
(58) Field of Classification Search ............. 250/559.4, 250/559.16, 559.41, 559.44, 559.22; 356/445, 356/446, 448  
See application file for complete search history.

(56) References Cited

U.S. PATENT DOCUMENTS 5,004,929 A * 4/1991 Kakinoki ............... 250/559.06

RE33,991 E * 7/1992 Shiba ...................... 356/237.3  
6,566,673 B1 * 5/2003 Swan ....................... 250/559.4  
6,914,684 B1 * 7/2005 Bolash ...................... 356/600

FOREIGN PATENT DOCUMENTS

JP           10-198174           7/1998  
JP           2001-180843         7/2001

* cited by examiner

*Primary Examiner*—Thanh X. Luu  
*Assistant Examiner*—Tony Ko  
(74) *Attorney, Agent, or Firm*—Nixon & Vanderhye P.C.

(57) ABSTRACT

An optical object identifying device has a light-emitting device, a first photodetector and a second photodetector. In the optical object identifying device, an angle of 10 to 30 degrees is formed between the optical axis of the light-emitting device and the surface of the sheet to be identified. Also, an angle of 10 to 30 degrees is formed between the optical axis of the first photodetector and the surface of the sheet. Further, an angle of approximately 90 degrees is formed between the optical axis of the second photodetector and the surface of the sheet. Thus, the light-emitting device, the first photodetector and the second photodetector are arranged in the optimum positions, so that the first photodetector and the second photodetector can obtain two output values varied with each of many types of sheets.

3 Claims, 7 Drawing Sheets

OPTICAL OBJECT IDENTIFYING DEVICE AND PRINTING APPARATUS

CROSS-REFERENCE TO RELATED APPLICATIONS

This nonprovisional application claims priority under 35 U.S.C. §119(a) on Patent Application No. 2003-315059 filed in Japan on 08 Sep. 2003, the entire contents of which are incorporated herein by reference.

BACKGROUND OF THE INVENTION

The present invention relates to an optical object identifying device that detects the type of an object in a noncontact manner and a printing apparatus that employs the device.

Generally, copiers and printers, which carry out recording processes while conveying recording media, have advanced in high-function, high-speed processing and high resolutions. The recording media to be used include a variety of types such as regular paper, glossy paper, OHP (Overhead Projector) sheets and so on. When printing is carried out on such a variety of types of recording media by a printer or the like (e.g., a printer of an ink-jet recording system), which is an image recording apparatus, it is required to form a high quality image by executing recording control in accordance with conditions of the recording medium, specifically, differences in the permeation rate and the time of drying of the ink depending on the type of the recording medium.

There are, for example, a first example of prior art and a second example of prior art as a device for detecting the types of the recording media of papers such as printing paper, resin films or sheets and so on.

Figure 10:
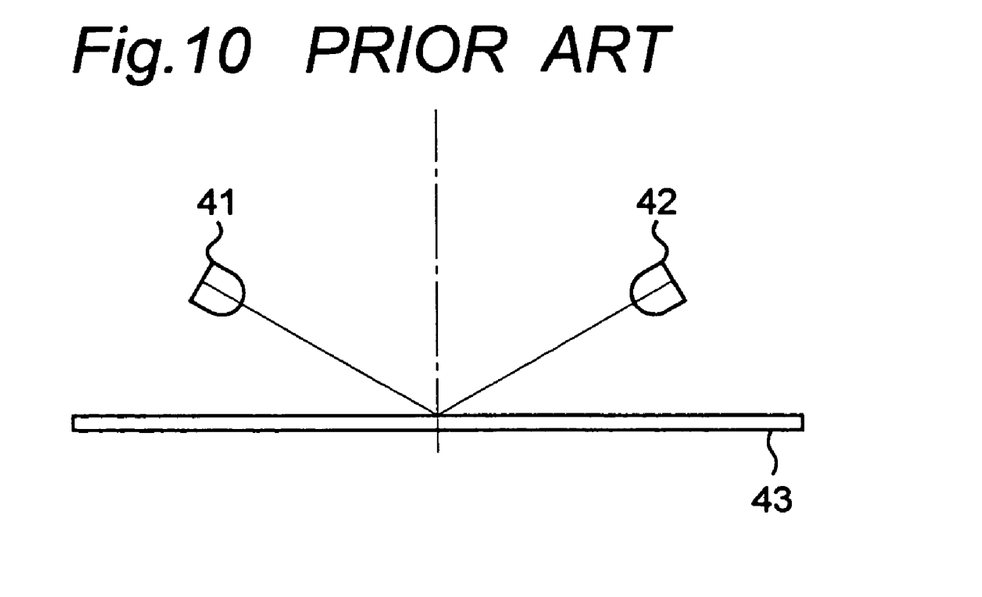
FIG. 10 is a schematic structural view showing a prior art optical object identifying device.

In the first example of prior art, as shown in FIG. 10, a light-emitting device 41 and a photodetector 42 have been arranged at a prescribed angle with respect to a sheet 43 in order to reflect light emitted from the light-emitting device 41 on the sheet 3, and then to enter part of this reflected light into the photodetector 42. The quantity of light incident on the photodetector 42 has differed depending on the type (surface condition) of the sheet 43, and therefore, the type of the sheet 43 has been identified on the basis of this difference. Reference should be made to, for example, JP 10-198174 A.

Figure 11:
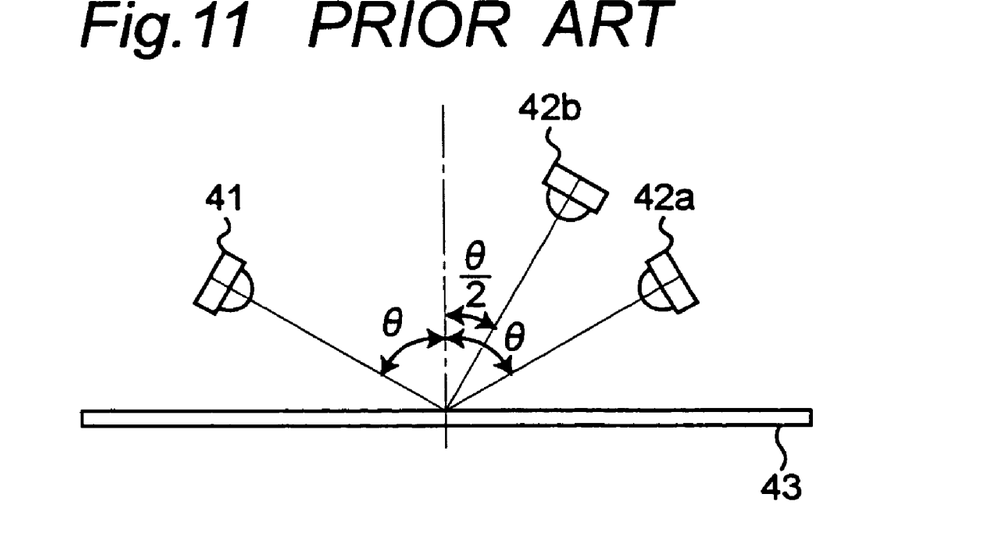
FIG. 11 is a schematic structural view showing another prior art optical object identifying device.

In the second example of prior art, as shown in FIG. 11, one light-emitting device 41 and two photodetectors 42a and 42b have been arranged at prescribed angles with respect to the sheet 43, respectively. Specifically, a light-emitting device 41 and a first photodetector 42a have been arranged at same angle θ with respect to a direction perpendicular to the sheet 43, and a second photodetector 42b has been arranged at an angle θ/2 which is a half of the angle θ of the first photodetector 42a. The first photodetector 42a has received regular reflection light from the sheet 43, and the second the photodetector 42b has received diffuse reflection light from the sheet 43. Then, the type of the sheet 43 has been identified by a variance in the value of the quantity of light incident on the two photodetectors 42a and 42b depending on the sheet 43. Reference should be made to, for example, JP 2001-180843 A.

However, there are various types of sheets including regular paper, glossy paper, OHP paper, mat paper, a luster film, an inkjet postcard and so on. Thus, it has been difficult for the above-stated first and second examples of prior art to accurately identify all these types. Only the three types of regular paper, glossy paper and OHP paper have been able to be identified at the most.

SUMMARY OF THE INVENTION

An object of the present invention is therefore to provide an optical object identifying device capable of easily identifying many types of objects by reflected light from an object to be detected and a printing apparatus that employs the device.

In order to solve the above-stated disadvantages, this invention provides an optical object identifying device comprising:

a light-emitting device;

a first photodetector and a second photodetector, which receive light reflected from a surface of an object to be detected after the light is applied from the light-emitting device to the surface of the object to be detected; and an identification means for identifying a type of the object to be detected on a basis of values of outputs outputted from the first photodetector and the second photodetector, wherein the light-emitting device and the first photodetector exist respectively on both sides of a normal line established at an intersection of an optical axis of the light-emitting device and the surface of the object to be detected, the light-emitting device is arranged such that an angle made between the optical axis of the light-emitting device and the surface of the object to be detected becomes 10 to 30 degrees, the first photodetector is arranged such that an angle made between an optical axis of the first photodetector and the surface of the object to be detected becomes 10 to 30 degrees, and the second photodetector is arranged such that an angle made between an optical axis of the second photodetector and the surface of the object to be detected becomes approximately 90 degrees.

It should be noted that the output values outputted from the first photodetector and the second photodetector each represents an output value obtained from an output signal of a waveform corresponding to surface roughness of the object to be detected. Further, on condition that the surface of the object to be detected is a uniform plane, there are determined the normal line, the angle made between and the optical axis of the light-emitting device and the surface of the object to be detected, the angle made between the optical axis of the first photodetector and the surface of the object to be detected and the angle made between the optical axis of the second photodetector and the surface of the object to be detected. Moreover, there coincide with one another the intersection of the optical axis of the light-emitting device and the surface of the object to be detected, the intersection of the optical axis of the first photodetector and the surface of the object to be detected and the intersection of the optical axis of the second photodetector and the surface of the object to be detected.

An equal angle within a range of 10 to 30 degrees should preferably be employed for the angle made between the optical axis of the light-emitting device and the surface of the object to be detected and the angle made between the optical axis of the first photodetector and the surface of the object to be detected.

According to the optical object identifying device of this invention, 10 to 30 degrees is employed as the angle made between the optical axis of the light-emitting device and the surface of the object to be detected, 10 to 30 degrees is employed as the angle made between the optical axis of the first photodetector and the surface of the object to be detected, and approximately 90 degrees is employed as the angle made between the optical axis of the second photodetector and the surface of the object to be detected. These make it possible to arrange in optimum positions the light-emitting device that emits light to the object to be detected, the first photodetector that receives the regular reflection light from the object to be detected and the second photodetector that receives the diffuse reflection light from the object to be detected. That is, with this arrangement, an output value varied for each of many types of objects to be detected can be obtained on the basis of the output values outputted from the first photodetector and the second photodetector. Thus, two output values (signals of two lines) varied for each of many types of sheets can be obtained in the case where there are many types of sheets of regular paper, mat paper, glossy paper, OHP paper, iron print paper and inkjet paper as the object to be detected, for example.

Therefore, many types of objects can easily be accurately identified by the reflected light from the object to be detected.

Moreover, in the optical object identifying device of one embodiment, the light-emitting device has a wavelength of not longer than 660 nm.

According to the optical object identifying device of this one embodiment, difference become large in the quantity of reflected light between many types of objects, and the output values varied for each of many types of objects can be obtained. Thereby, it becomes possible to achieve highly accurate identification.

Moreover, the optical object identifying device of one embodiment further comprises polarizing plates provided respectively on the optical axis of the light-emitting device, on the optical axis of the first photodetector and on the optical axis of the second photodetector, wherein light polarized through the polarizing plates passes in a direction perpendicular to an imaginary plane formed of the optical axis of the light-emitting device, the optical axis of the first photodetector and the optical axis of the second photodetector.

According to the optical object identifying device of this one embodiment, it becomes easy to identify the object, or the object to be detected by virtue of the provision of the polarizing plates. This optical object identifying device utilizes whether this polarized state can keep or breaks down depending on the surface condition of the object to be detected when the polarized light in the direction perpendicular to the imaginary plane is reflected on the object to be detected. That is, if this polarized state can be kept, then the polarized light reflected on the object to be detected reaches the photodetectors through the polarizing plates arranged on the optical axes of the photodetectors. However, if this polarized state cannot be kept, then only part of the light reflected on the object to be detected reaches the photodetectors. In this way, the optical object identifying device utilizes the phenomenon that the quantities of light incident on the photodetectors change depending on the difference in the surface condition of the object to be detected.

Moreover, the optical object identifying device of one embodiment, further comprises:

a first polarizing plate provided on the optical axis of the light-emitting device, wherein light polarized through the first polarizing plate passes in a direction perpendicular to an imaginary plane formed of the optical axis of the light-emitting device, the optical axis of the first photodetector and the optical axis of the second photodetector;

a second polarizing plate provided on the optical axis of the first photodetector, wherein light polarized through the second polarizing plate passes in a direction rotated by a prescribed angle around the optical axis of the first photodetector from a direction perpendicular to the imaginary plane; and a third polarizing plate provided on the optical axis of the second photodetector, wherein light polarized through the third polarizing plate passes in a direction rotated by a prescribed angle around the optical axis of the second photodetector from a direction perpendicular to the imaginary plane.

The prescribed angle should preferably be 30 to 60 degrees.

According to the optical object identifying device of this one embodiment, it becomes easy to identify the object, or the object to be detected, by virtue of the provision of the first polarizing plate, the second polarizing plate and the third polarizing plate. This optical object identifying device utilizes whether or not the light becomes polarized light rotated by the prescribed angle from the direction perpendicular to the imaginary plane depending on the surface condition of the object to be detected when the polarized light in the direction perpendicular to the imaginary plane is reflected on the object to be detected. That is, if the light becomes the polarized light rotated by the prescribed angle, then the polarized light reflected on the object to be detected passes through the polarizing plates arranged on the optical axes of the photodetectors and reaches the photodetectors. However, if the light does not become the polarized light rotated by the prescribed angle, then only part of the light reflected on the object to be detected reaches the photodetectors. As described above, the optical object identifying device utilizes the phenomenon that the quantities of light incident on the photodetectors change depending on the difference in the surface condition of the object to be detected.

Moreover, the optical object identifying device of one embodiment further comprises slits for limiting travel paths of light provided respectively on a light-emitting side of the light-emitting device, on a light-receiving side of the first photodetector and on a light-receiving side of the second photodetector.

According to the optical object identifying device of this one embodiment, by virtue of the provision of the slits, the region of the light spot, which is formed on the surface of the object to be detected by light applied from the light-emitting device, can be conscribed to a region that does not excessively expand from the intersection of the optical axis of the light-emitting device and the surface of the object to be detected. Therefore, almost only the light of the regular reflection component can be made incident on the first photodetector, and the accuracy of the output value outputted from the first photodetector is improved. If the region of the light spot becomes enlarged, then the first photodetector disadvantageously receives the light other than the regular reflection component even if the angle made between the optical axis of the light-emitting device and the surface of the object to be detected is made equal to the angle made between the optical axis of the first photodetector and the surface of the object to be detected. Thus, the output value is degraded in accuracy.

Moreover, the optical object identifying device of one embodiment further comprises a collimating lens provided on a light-emitting side of the light-emitting device.

According to the optical object identifying device of this one embodiment, by virtue of the provision of the collimating lens, parallel light can be applied from the light-emitting device to the object to be detected, and the region of the light spot, which is formed on the surface of the object to be detected by light applied from the light-emitting device, can be conscribed to a region that does not excessively expand from the intersection of the optical axis of the light-emitting device and the surface of the object to be detected. Therefore, almost only the light of the regular reflection component can be made incident on the first photodetector, and the accuracy of the output value outputted from the first photodetector is improved. If the region of the light spot becomes enlarged, then the first photodetector disadvantageously receives the light other than the regular reflection component even if the angle made between the optical axis of the light-emitting device and the surface of the object to be detected is made equal to the angle made between the optical axis of the first photodetector and the surface of the object to be detected, and the accuracy of the output value is degraded.

Moreover, in the optical object identifying device of one embodiment, the light-emitting device is a semiconductor laser.

According to the optical object identifying device of this one embodiment, the semiconductor laser that can be regarded almost as a point light source is employed for the light-emitting device, and therefore, the region of the light spot can be further reduced in size, and the accuracy can be further improved.

Moreover, in the optical object identifying device of one embodiment, the identification means calculates A/B and identifies the type of the object to be detected by the calculation value, where A is an output value of the first photodetector, and B is an output value of the second photodetector.

According to the optical object identifying device of this one embodiment, the identification means identifies the type of the object to be detected by the calculation value of A/B, and therefore, many types can be accurately identified.

Moreover, in the optical object identifying device of one embodiment, the identification means calculates (A+B)/(A−B) and identifies the type of the object to be detected by the calculation value, where A is an output value of the first photodetector, and B is an output value of the second photodetector.

According to the optical object identifying device of this one embodiment, the identification means identifies the type of the object to be detected by the calculation value of (A+B)/(A−B), and therefore, many types can be accurately identified.

It is to be noted that the identification means may obtain the calculation values of both the calculation value of A/B and the calculation value of (A+B)/(A−B), by which much more types can be accurately identified.

Moreover, in the optical object identifying device of one embodiment, the identification means calibrates the output value of the first photodetector and the output value of the second photodetector before obtaining the calculation value.

In this case, the calibration is defined as an operation of adjusting the output values so that the values do not vary with each type of the optical object identifying device (identification means).

According to the optical object identifying device of this one embodiment, many types of objects can be accurately identified by obviating the need for considering variations in the light-emitting efficiency of the light-emitting device and variations in the sensitivity of the photodetectors and preventing the calculation value from varying with each type of the optical object identifying device (identification means).

Moreover, the present invention provides a printing apparatus provided with the above-stated optical object identifying device.

According to the printing apparatus of this invention, correct identification can be achieved by providing the optical object identifying device even if there are many types of sheets and films of the objects to be subjected to printing, and therefore, high-quality printing can be achieved on an optimum printing condition corresponding to each of the types.

BRIEF DESCRIPTION OF THE DRAWINGS

The present invention will become more fully understood from the detailed description given hereinbelow and the accompanying drawings which are given by way of illustration only, and thus are not limitative of the present invention, and wherein.

DETAILED DESCRIPTION OF THE PREFERRED EMBODIMENTS

The present invention will be described in detail below on the basis of embodiments thereof shown in the drawings.

First Embodiment

Figure 1:
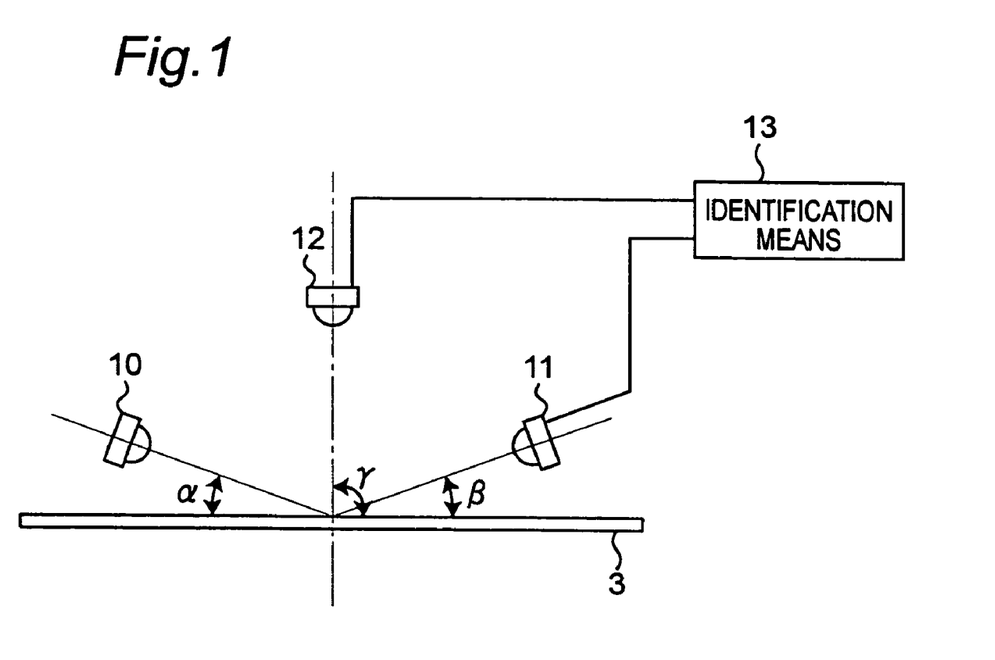
FIG. 1 is a schematic structural view showing an optical object identifying device according to a first embodiment of the present invention.

FIG. 1 shows a schematic structural view showing an optical object identifying device according to a first embodiment of the present invention. This optical object identifying device has a light-emitting device 10, a first photodetector 11, a second photodetector 12 and identification means 13.

The first photodetector 11 and the second photodetector 12 receive reflected light from the surface of a sheet 3 caused by applying light from the light-emitting device 10 to the surface of the sheet 3. The identification means 13 identifies the type of the sheet 3 on the basis of output values outputted from the first photodetector 11 and the second photodetector 12.

As the sheet 3, there are, for example, regular paper, mat paper, glossy paper, OHP paper, iron print paper, inkjet paper, and so on.

The output value of the first photodetector 11 and the output value of the second photodetector 12 are each the output value obtained from an output signal of a waveform corresponding to the surface roughness of the sheet 3.

The light-emitting device 10 and the first photodetector 11 exist on both sides of a normal line established at the intersection of the optical axis of this light-emitting device 10 and the surface of the sheet 3.

The light-emitting device 10 is arranged such that an angle α made between the optical axis of this light-emitting device 10 and the surface of the sheet 3 becomes 10 to 30 degrees, and emits light to the sheet 3.

The first photodetector 11 is arranged such that an angle β made between the optical axis of this first photodetector 11 and the surface of the sheet 3 becomes 10 to 30 degrees, and receives regular reflection light from the sheet 3. The angle α and the angle β are preferably equal to each other.

The second photodetector 12 is arranged such that an angle γ made between the optical axis of this second photodetector 12 and the surface of the sheet 3 becomes approximately 90 degrees, and receives diffuse reflection light from the sheet 3.

According to the optical object identifying device having the above-mentioned construction, an output value varied in accordance with each type of the sheet 3 can be obtained from the output values outputted from the first photodetector 11 and the second photodetector 12 because the light-emitting device 10, the first photodetector 11 and the second photodetector 12 are arranged in the optimum positions. Therefore, many types of sheets 3 can easily be accurately identified by the reflected light from the sheet 3.

The wavelength of the light-emitting device 10 is not longer than 660 nm, and differences in the quantity of reflected light between many types of the sheets 3 become large. This makes it possible to obtain the output values varied in accordance with each of many types of sheets 3, and therefore, to achieve highly accurate identification. In addition, the wavelength of the light-emitting device 10 may be within the infrared region.

Second Embodiment

Figure 2A:
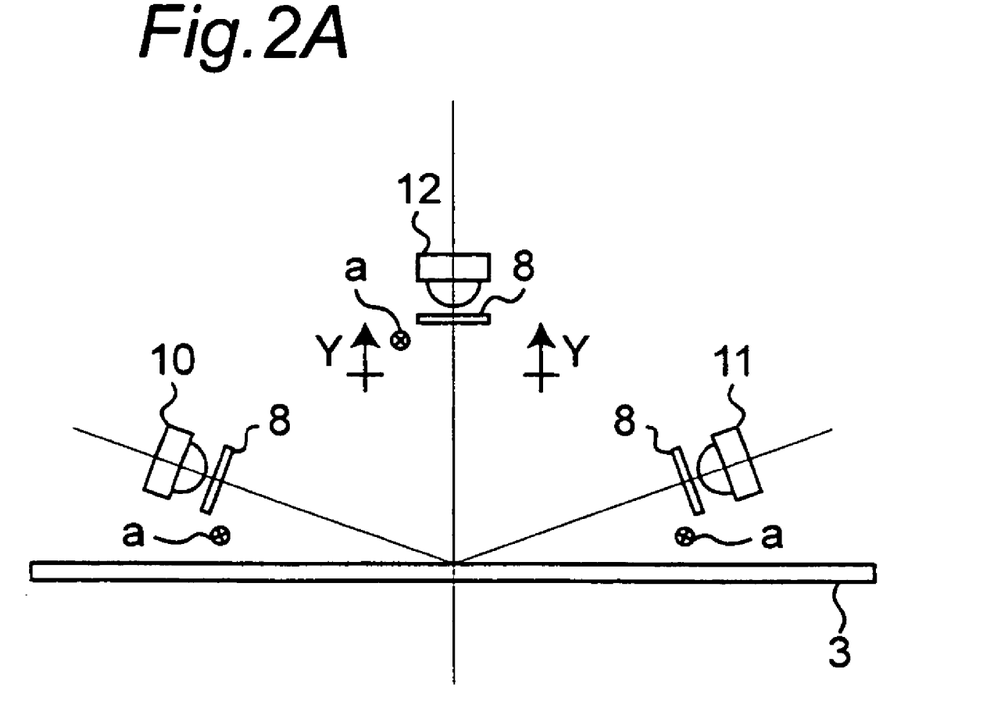
FIG. 2A is a schematic structural view showing an optical object identifying device according to a second embodiment of the present invention.
Figure 2B:
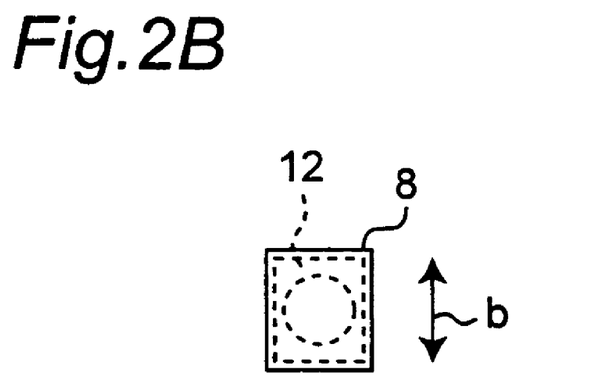
FIG. 2B is a schematic structural view showing part of the optical object identifying device according to the second embodiment of the present invention.

FIGS. 2A and 2B show an optical object identifying device according to a second embodiment of the present invention. FIG. 2A shows a schematic structural view of this optical object identifying device. FIG. 2B shows a view taken along the arrow line Y—Y of FIG. 2A.

In this optical object identifying device, polarizing plates 8 are provided on the optical axis of the light-emitting device 10, the optical axis of the first photodetector 11 and the optical axis of the second photodetector 12, respectively. The polarizing plate 8 allows polarized light to pass in a direction perpendicular to an imaginary plane which is formed of the optical axis of the light-emitting device 10, the optical axis of the first photodetector 11 and the optical axis of the second photodetector 12. Description of other structures than the above is omitted since the other structure is the same as that of the first embodiment.

The imaginary plane coincides with the sheet plane of FIG. 2A. The perpendicular direction represents the direction of arrow "a" which is perpendicular to the sheet plane in FIG. 2A, and represents the direction of arrow "b" in FIG. 2B.

According to the optical object identifying device having the above-mentioned construction, it becomes easy to identify the sheet 3 by virtue of the provision of the polarizing plates 8. Particularly, the polarizing plates 8 become more effective when the wavelength of the light-emitting device 10 is not longer than 660 nm.

Specifically, this optical object identifying device utilizes whether or not the polarized state can keep or break down depending on the surface condition of the sheet 3 when the polarized light in the direction perpendicular to the imaginary plane is reflected on the sheet 3. That is, if the polarized state can be kept, then the polarized light reflected on the sheet 3 reaches the photodetectors 11 and 12 through the polarizing plates 8 arranged on the optical axes of the photodetectors 11 and 12. If the polarized state cannot be kept, then only part of the light reflected on the sheet 3 reaches the photodetectors 11 and 12. As described above, the optical object identifying device utilizes the phenomenon that the quantities of light incident on the photodetectors 11 and 12 change depending on the difference in the surface condition of the sheet 3.

Third Embodiment

Figure 3A:
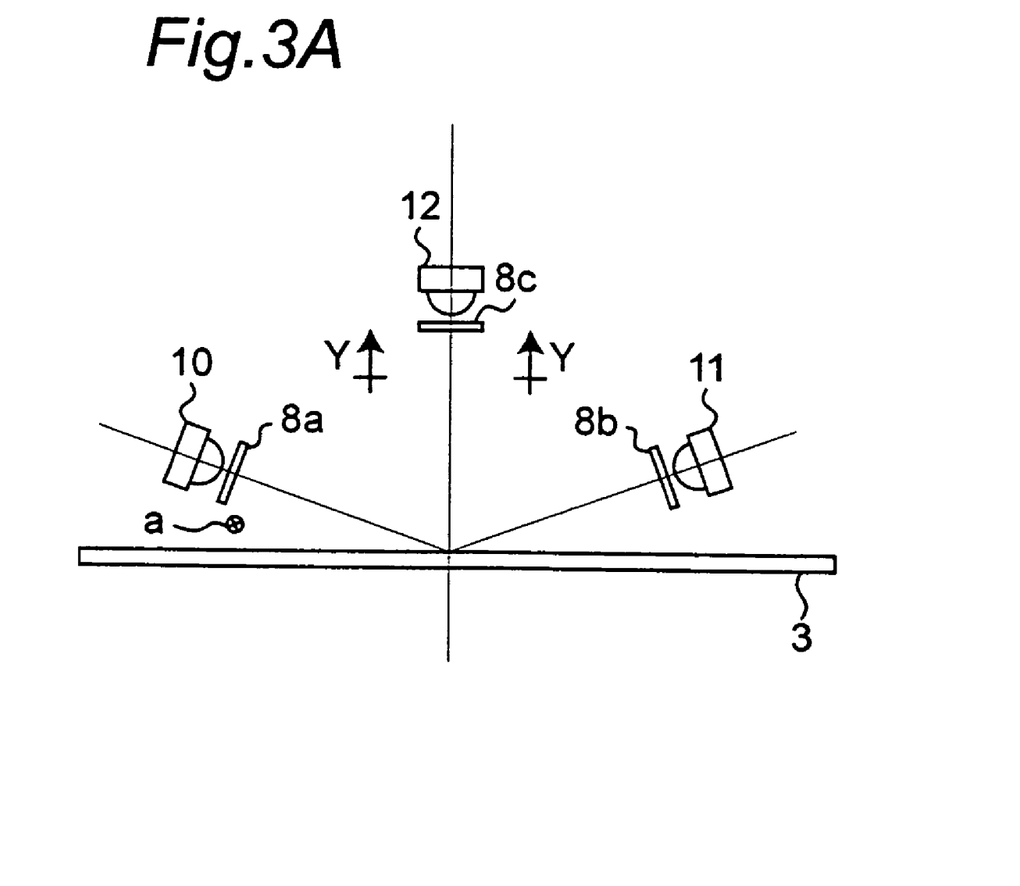
FIG. 3A is a schematic structural view showing an optical object identifying device according to a third embodiment of the present invention.
Figure 3B:
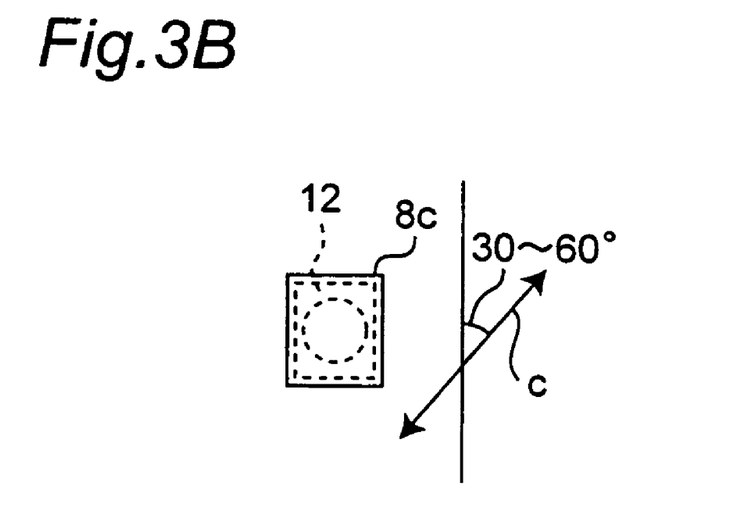
FIG. 3B is a schematic structural view showing part of the optical object identifying device according to the third embodiment of the present invention.

FIGS. 3A and 3B show an optical object identifying device according to another embodiment of the present invention. FIG. 3A shows a schematic structural view of this optical object identifying device. FIG. 3B shows a view taken along the arrow line Y—Y of FIG. 3A.

In this optical object identifying device, a first polarizing plate 8a is provided on the optical axis of the light-emitting device 10. The first polarizing plate 8a allows polarized light to pass in the direction perpendicular to the above-stated imaginary plane. Also, a second polarizing plate 8b is provided on the optical axis of the first photodetector 11. The second polarizing plate 8b passes polarized light rotated by a prescribed angle around the optical axis of the first photodetector 11 from the direction perpendicular to the imaginary plane. Further, a third polarizing plate 8c is provided on the optical axis of the second photodetector 12. The third polarizing plate 8c passes polarized light rotated by a prescribed angle around the optical axis of the second photodetector 12 from the direction perpendicular to the imaginary plane. Description of other structure than the above is omitted since the other structure is the same as that of the first embodiment.

The imaginary plane coincides with the sheet plane of FIG. 3A. The perpendicular direction represents the direction of arrow "a" which is perpendicular to the sheet plane in FIG. 3A. The direction of polarized light that passes through the third polarizing plate 8c represents the direction of arrow "c" in FIG. 3B. Although the prescribed angle rotated from the perpendicular direction is 30 to 60 degrees, the angle may be another angle.

According to the optical object identifying device having the above-mentioned construction, it becomes easy to identify the sheet 3 by virtue of the provision of the first polarizing plate 8a, the second polarizing plate 8b and the third polarizing plate 8c. Particularly, when the wavelength of the light-emitting device 10 is not longer than 660 nm, the construction is effective.

Specifically, the above-mentioned optical object identifying device utilizes whether or not the polarized light is rotated by the prescribed angle from the direction perpendicular to the imaginary plane depending on the surface condition of the sheet 3 when the polarized light in the direction perpendicular to the imaginary plane is reflected on the sheet 3. That is, if the polarized light is rotated by the prescribed angle, then the polarized light reflected on the sheet 3 passes through the polarizing plates 8b and 8c arranged on the optical axes of the photodetectors 11 and 12 and reaches the photodetectors 11 and 12. However, if the polarized light is rotated by the prescribed angle, then only part of the light reflected on the sheet 3 reaches the photodetectors 11 and 12. As described above, the optical object identifying device utilizes the phenomenon that the quantities of light incident on the photodetectors change depending on the difference in the surface condition of the sheet 3.

Fourth Embodiment

Figure 4:
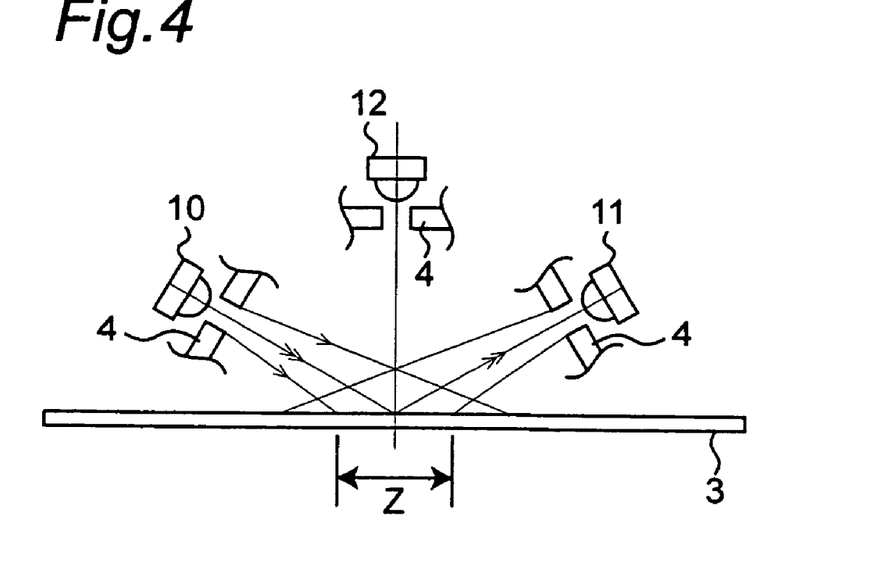
FIG. 4 is a schematic structural view showing an optical object identifying device according to a fourth embodiment of the present invention.

FIG. 4 shows an optical object identifying device according to another embodiment of the present invention. In this optical object identifying device, slits 4 that limit the travel paths of light are provided respectively on the light-emitting sides of the light-emitting device 10, the first photodetector 11 and the second photodetector 12. Since the other structure is the same as that of the first embodiment, no description is provided therefor.

According to the optical object identifying device having the above-mentioned construction, by virtue of the provision of the slits 4, the region Z of the light spot, which is formed on the surface of the sheet 3 by light applied from the light-emitting device 10, can be conscribed to a region that does not excessively expand from the intersection of the optical axis of the light-emitting device 10 and the surface of the sheet 3. Therefore, almost only the light of the regular reflection component can be made incident on the first photodetector 11, and the accuracy of the output value outputted from the first photodetector 11 is improved.

Figure 5:
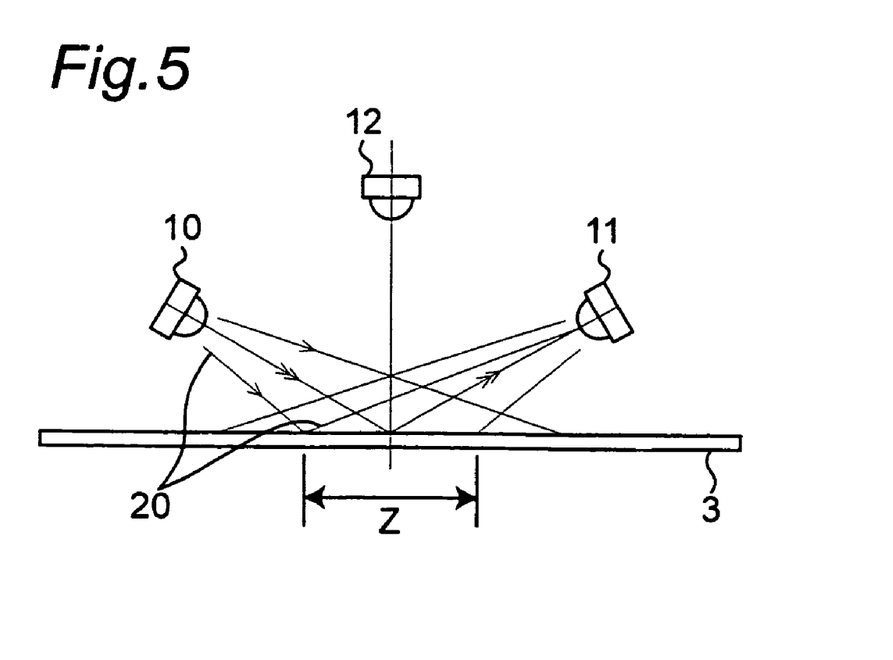
FIG. 5 is a schematic structural view showing a comparative example of the optical object identifying devices according to the present invention.

In the case of no slit 4, the region Z of the light spot becomes enlarged as shown in FIG. 5. Therefore, the first photodetector 11 disadvantageously receives the light other than the regular reflection component even if the angle made between the optical axis of the light-emitting device 10 and the surface of the sheet 3 is made equal to the angle made between the optical axis of the first photodetector 11 and the surface of the sheet 3. Specifically, a ray of light (diffuse reflection light) 20, the incidence angle of which is different from the reflective angle thereof, is incident on the first photodetector 11. Thus, the value of the output outputted from the first photodetector 11 becomes degraded in accuracy.

Fifth Embodiment

Figure 6:
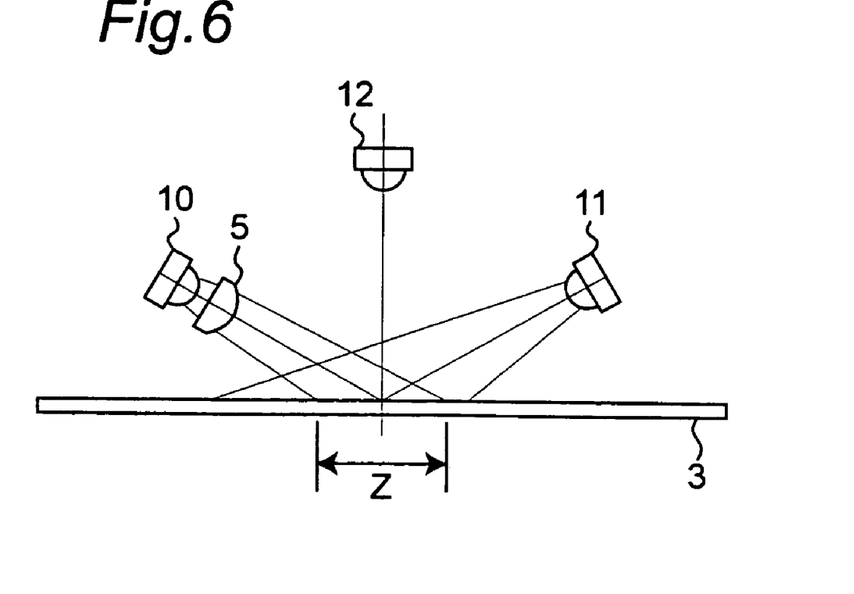
FIG. 6 is a schematic structural view showing an optical object identifying device according to a fifth embodiment of the present invention.

FIG. 6 shows an optical object identifying device according to another embodiment of the present invention. In this optical object identifying device, a collimating lens 5 is provided on the light-emitting side of the light-emitting device 10 in place of the slits 4 of the fourth embodiment (FIG. 4). Since the other structure is the same as that of the first embodiment, no description is provided therefor.

According to the optical object identifying device having the above-mentioned construction, the collimating lens 5 allows light from the light-emitting device 10 to be parallel applied to the sheet 3. Therefore, the light spot region Z can be reduced in size. Thus, almost only the light of the regular reflection component can be made incident on the first photodetector 11, and the value of the output outputted from the first photodetector 11 is improved in accuracy.

It is to be noted that the degree of parallelism of the parallel light from the collimating lens 5 can be improved in order to further reduce the size of the light spot region Z.

Sixth Embodiment

Figure 7:
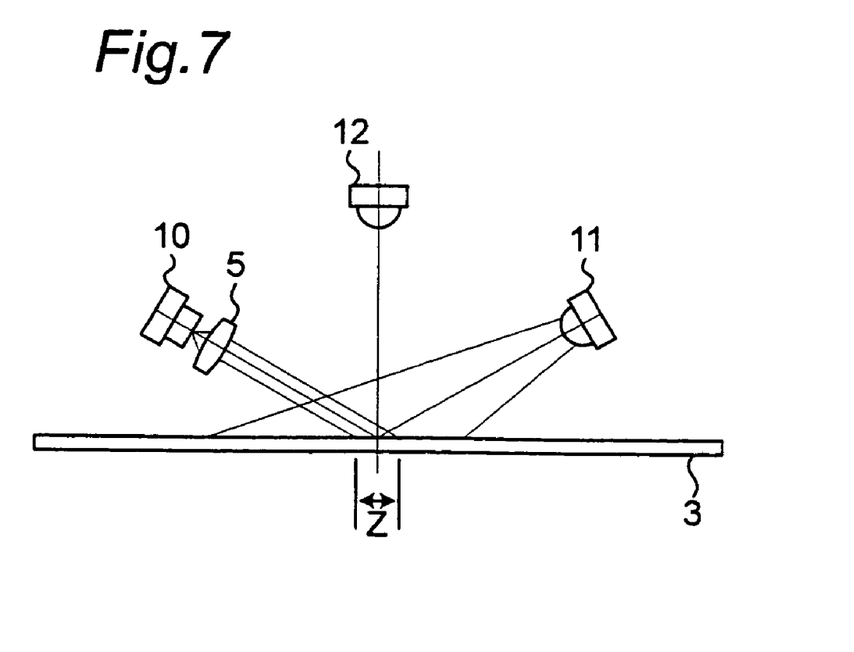
FIG. 7 is a schematic structural view showing an optical object identifying device according to a sixth embodiment of the present invention.

FIG. 7 shows an optical object identifying device according to still another embodiment of the present invention. In this optical object identifying device, a semiconductor laser is employed for the light-emitting device 10 in addition to the collimating lens 5 of the fifth embodiment (FIG. 6). Since the other structure is the same as that of the first embodiment, no description is provided therefor.

According to the optical object identifying device having the above-mentioned construction, the semiconductor laser that can be regarded almost as a point light source is employed for the light-emitting device 10, and therefore, the light spot region Z can be further reduced in size, and the accuracy can be further improved.

Seventh Embodiment

Figure 8:
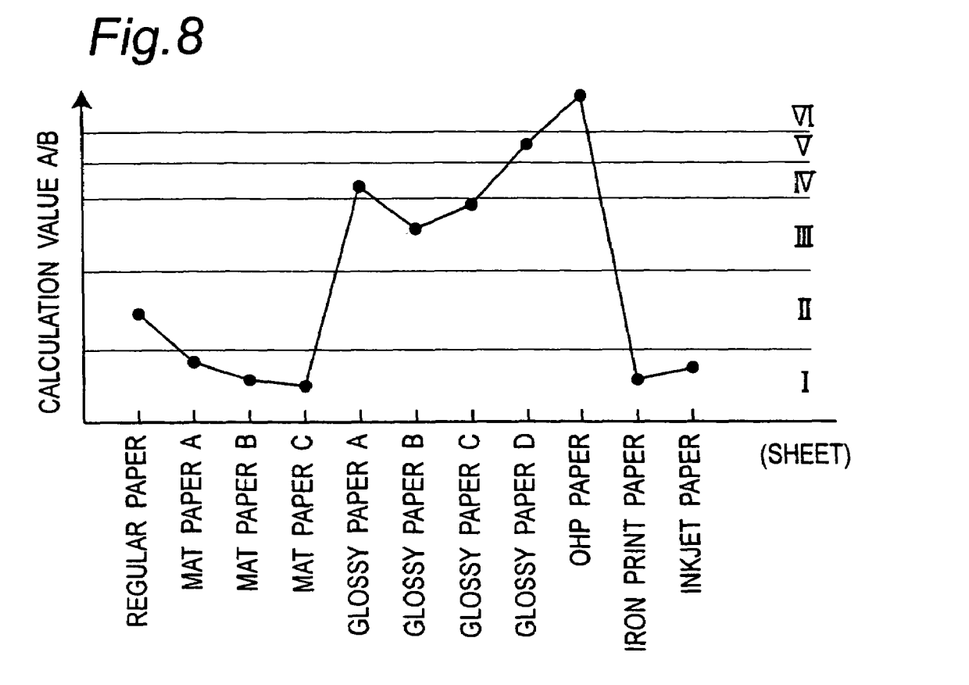
FIG. 8 is a graph showing types of sheets plotted on a horizontal axis and calculation values plotted on a vertical axis.

FIG. 8 is a graph showing calculation values calculated for each type of the sheet 3 by the identification means 13 on the basis of the output values of the photodetectors 11 and 12. Assuming that the output value of the first photodetector 11 is A and that the output value of the second photodetector 12 is B, then the identification means 13 calculates A/B and identifies the type of the sheet 3 by this calculation value.

Specifically, as the types of the sheet 3, there are regular paper, three types of mat paper, four types of glossy paper, OHP paper, iron print paper and inkjet paper, and the sheets can be classified (identified) into six groups of I through VI by the calculation value of A/B. That is, the sheet types other than iron print paper, inkjet paper and mat paper can be identified.

Eighth Embodiment

Figure 9:
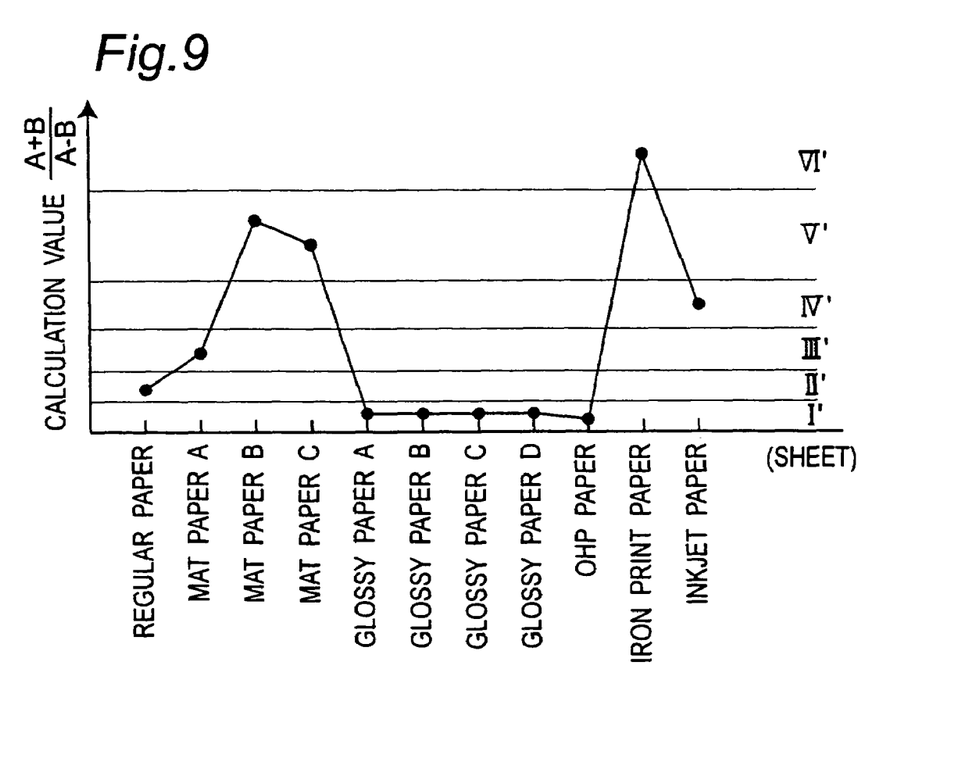
FIG. 9 is another graph showing the types of sheets plotted on a horizontal axis and calculation values plotted on a vertical axis.

FIG. 9 is a graph showing calculation values calculated for each type of the sheet 3 by the identification means 13 on the basis of the output values of the photodetectors 11 and 12. Assuming that the output value of the first photodetector 11 is A and that the output value of the second photodetector 12 is B, then the identification means 13 calculates $(A+B)/(A-B)$ and identifies the type of the sheet 3 by this calculation value.

Specifically, as the types of the sheet 3, there are regular paper, three types of mat paper, four types of glossy paper, OHP paper, iron print paper and inkjet paper, and the sheets can be classified (identified) into six groups of I' through VI' by the calculation value of $(A+B)/(A-B)$. That is, sheet types other than iron print paper, inkjet paper and mat paper can be identified.

Ninth Embodiment

The identification means 13 may obtain the calculation values of both the calculation value of A/B and the calculation value of (A+B)/(A−B), by which the sheet types other than glossy paper B, glossy paper C, mat paper B and mat paper C shown in FIGS. 8 and 9 can be identified.

Tenth Embodiment

The identification means 13 may carry out calibration of the output value A of the first photodetector 11 and the output value B of the second photodetector 12 before obtaining the calculation value.

In this case, the calibration is defined as an operation of adjusting the output values A and B so that the values do not vary with each type of the optical object identifying device (identification means 13).

According to the optical object identifying device having the above-mentioned construction, many types of sheets 3 can be accurately identified by obviating the need for considering variations in the light-emitting efficiency of the light-emitting device 10 and variations in the sensitivity of the photodetectors 11 and 12 and preventing the calculation value from varying with each type of the optical object identifying device (identification means 13).

Moreover, if this calibration is carried out, the variations in the calculation value are reduced. Therefore, sheets of a small difference in the calculation value or, for example, the glossy paper B and the glossy paper C shown in FIGS. 8 and 9 can be identified.

Eleventh Embodiment

Next, although not shown, the printing apparatus of this invention is provided with the optical object identifying device according to the above-stated embodiments.

According to the printing apparatus of this invention, in which one of the above-stated optical object identifying devices is provided, the sheet 3 can be identified so that printing can be carried out on an optimum printing condition corresponding to the type of the sheet 3.

The invention being thus described, it will be obvious that the invention may be varied in many ways. Such variations are not be regarded as a departure from the spirit and scope of the invention, and all such modifications as would be obvious to one skilled in the art are intended to be included within the scope of the following claims.

What is claimed is:

1. An optical object identifying device comprising:
  a light-emitting device;
  a first photodetector and a second photodetector, which receive light reflected from a surface of an object to be detected after the light is applied from the light-emitting device to the surface of the object to be detected; and
  an identification means for identifying a type of the object to be detected on a basis of values of outputs outputted from the first photodetector and the second photodetector, wherein
  the light-emitting device and the first photodetector exist respectively on both sides of a normal line established at an intersection of an optical axis of the light-emitting device and the surface of the object to be detected,
  the light-emitting device is arranged such that an angle made between the optical axis of the light-emitting device and the surface of the object to be detected becomes 10 to 30 degrees,
  the first photodetector is arranged such that an angle made between an optical axis of the first photodetector and the surface of the object to be detected becomes 10 to 30 degrees,
  the second photodetector is arranged such that an angle made between an optical axis of the second photodetector and the surface of the object to be detected becomes approximately 90 degrees so that the second photodetector receives at least light that leaves the surface of the object at an angle of approximately 90 degrees relative to the surface of the object; and
  wherein, the identification means calculates (A+B)/(A−B) and identifies the type of the object to be detected by the calculation value, where
  A is an output value of the first photodetector, and
  B is an output value of the second photodetector.

2. The optical object identifying device of claim 1, wherein the type of object to be identified is regular paper, mat paper, a group of glossy paper and OHP paper, iron print paper and inkjet paper.

3. An optical object identifying device comprising:
  a light-emitting device;
  a first photodetector and a second photodetector, which receive light reflected from a surface of an object to be detected after the light is applied from the light-emitting device to the surface of the object to be detected; and
  an identification means for identifying a type of the object to be detected on a basis of values of outputs outputted from the first photodetector and the second photodetector, wherein
  the light-emitting device and the first photodetector exist respectively on both sides of a normal line established at an intersection of an optical axis of the light-emitting device and the surface of the object to be detected,
  the light-emitting device is arranged such that an angle made between the optical axis of the light-emitting device and the surface of the object to be detected becomes 10 to 30 degrees,
  the first photodetector is arranged such that an angle made between an optical axis of the first photodetector and the surface of the object to be detected becomes 10 to 30 degrees,
  the second photodetector is arranged such that an angle made between an optical axis of the second photodetector and the surface of the object to be detected becomes approximately 90 degrees so that the second photodetector receives at least light that leaves the surface of the object at an angle of approximately 90 degrees relative to the surface of the object; and
  wherein:
  the identification means calculates A/B and (A+B)/(A−B), where A is an output value of the first photodetector, and B is an output value of the second photodetector, and
  values of the calculation are used to identify sheet types of regular paper, mat paper, glossy paper, OHP paper, iron print paper and inkjet paper.

* * * * *